United States Patent
Tg et al.

(10) Patent No.: US 10,308,583 B2
(45) Date of Patent: Jun. 4, 2019

(54) COMPOSITIONS COMPRISING SHIKIMIC ACID OBTAINED FROM OIL PALM-BASED MATERIALS

(71) Applicant: MALAYSIAN PALM OIL BOARD, Kajang, Selangor (MY)

(72) Inventors: Sambandan Tg, Uxbridge, MA (US); Chokyun Rha, Boston, MA (US); Ravigadevi Sambanthamurthi, Selangor (MY); Anthony J. Sinskey, Boston, MA (US); Yew Ai Tan, Kuala Lumpur (MY); Kalyana Sundram P. Manickam, Selangor Darul Ehsan (MY); Mohd Basri Wahid, Selangor Darul Ehsan (MY)

(73) Assignee: MALAYSIAN PALM OIL BOARD (MY)

( * ) Notice: Subject to any disclaimer, the term of this patent is extended or adjusted under 35 U.S.C. 154(b) by 0 days.

(21) Appl. No.: 15/943,777

(22) Filed: Apr. 3, 2018

(65) Prior Publication Data

US 2018/0222837 A1  Aug. 9, 2018

Related U.S. Application Data

(62) Division of application No. 15/414,058, filed on Jan. 24, 2017, now Pat. No. 9,963,415, which is a division of application No. 13/704,616, filed as application No. PCT/MY2011/000097 on Jun. 16, 2011, now abandoned.

(30) Foreign Application Priority Data

Jun. 16, 2010 (MY) .......................... PI/2010/02835

(51) Int. Cl.
*A61K 31/19* (2006.01)
*C07C 51/50* (2006.01)
*C07C 51/48* (2006.01)
*C07C 51/42* (2006.01)
*C12N 9/10* (2006.01)

(52) U.S. Cl.
CPC .............. *C07C 51/50* (2013.01); *C07C 51/42* (2013.01); *C07C 51/48* (2013.01); *C12N 9/1092* (2013.01); *C12Y 205/01019* (2013.01); *C07C 2601/16* (2017.05)

(58) Field of Classification Search
CPC ...................................................... A61K 31/19
USPC ......................................................... 514/568
See application file for complete search history.

(56) References Cited

U.S. PATENT DOCUMENTS 9,963,415 B2 * 5/2018 Tg .................. C12Y 205/01019
2007/0148266 A1 6/2007 Yan et al.

FOREIGN PATENT DOCUMENTS

| EP | 2106698 A2 | 10/2009 |
| WO | 2005/051103 A1 | 6/2005 |
| WO | 2007/109600 A2 | 9/2007 |
| WO | 2010/137943 A1 | 12/2010 |

OTHER PUBLICATIONS

International Search Report corresponding to Application No. PCT/MY2011/000097, dated Nov. 9, 2011.

* cited by examiner

*Primary Examiner* — Raymond J Henly, III
(74) *Attorney, Agent, or Firm* — Coeus Intellectual Property

(57) ABSTRACT

The present invention provides compositions and method for production of shikimic acid based on extracts obtained from oil palm-based materials, and more particularly oil palm-based waste materials and by-products. The method includes purifying shikimic acid from extracts comprising oil palm phenolics (OPP).

4 Claims, 1 Drawing Sheet

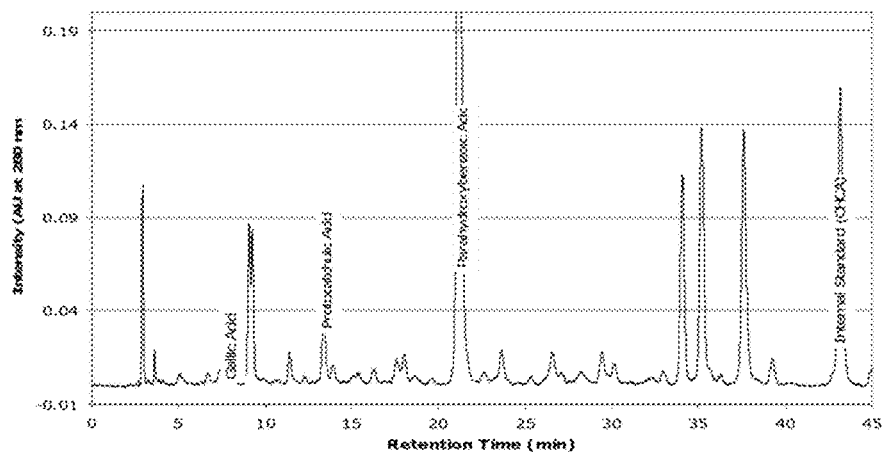
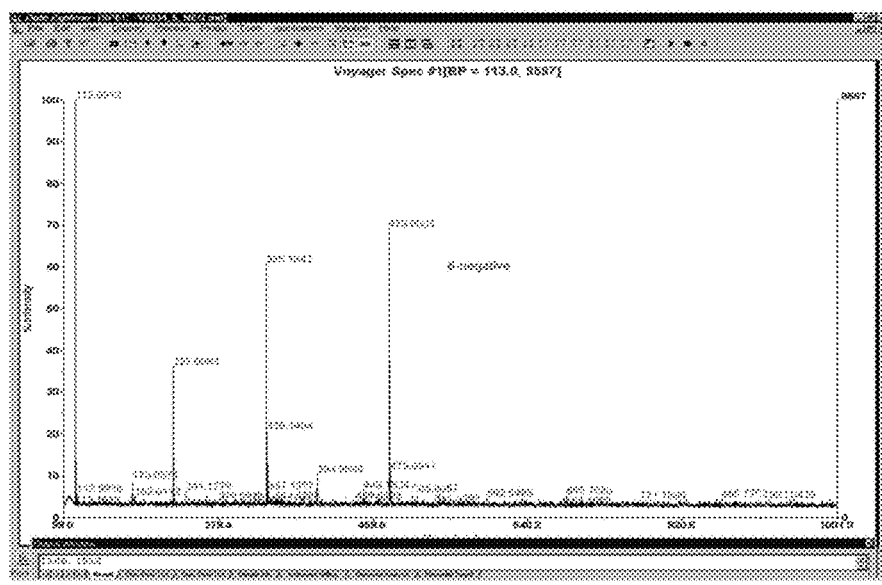

COMPOSITIONS COMPRISING SHIKIMIC ACID OBTAINED FROM OIL PALM-BASED MATERIALS

CROSS-REFERENCE TO RELATED APPLICATIONS

This application is a divisional of U.S. application Ser. No. 15/414,058 filed on Jan. 24, 2017, now U.S. Pat. No. 9,963,415, which is a divisional of U.S. application Ser. No. 13/704,616 filed on Mar. 4, 2013, abandoned, which is a National Stage Entry of International App. No. PCT/MY2011/000097 filed on Jun. 16, 2011, which claims priority to Malaysian App. No. PI/2010/02835 filed on Jun. 16, 2010; and which applications are incorporated herein by reference in their entireties.

FIELD OF INVENTION

The invention generally relates to a method to obtain and produce shikimic acid from plants and plant-based materials, and more particularly to a method for producing shikimic acid based on oil palm and oil palm-based materials.

BACKGROUND OF THE INVENTION

Reference to any prior art in this specification is not, and should not be taken as, an acknowledgement or any form of suggestion that this prior art forms part of the common general knowledge in Malaysia or any other country.

Shikimic Acid (SA) is an imperative biochemical intermediate in plants and microorganisms and has emerged as a vital starting material in the synthesis of an anti-influenza drug, widely known as Tamiflu (oseltamivir). It is discovered to be highly functionalized and it plays a major role in the production of essential aromatic amino acids which are not synthesized in the human body, such as phenylalanine, tryptophan and tyrosine. Presently, shikimic acid can be obtained based on microbe-catalyzed synthesis schemes or from plants, whereby the primary plant-based source for shikimic acid is the star anise (*Illicium anisatum*), whereby the yield of shikimic acid from star anise seed can be as high as 7%.

Oseltamivir, also known as the trade name Tamiflu, aids in the treatment and prophylaxis of both influenza virus A and influenza virus B infection, by way of blocking the influenza virus from spreading between cells and body. The administration of oseltamivir is preferably conducted within 48 hours from the first appearance of flu symptoms, as during this period it is observed that the virus has yet to replicate and infect many cells thus inhibition is considerably more effective. Under normal circumstances, the compound from Tamiflu is hydrolyzed by esterase in the liver, forming active form of drug, which is the oseltamivir carboxylate. Oseltamivir carboxylate then binds to and thereby inhibits viral neuraminidase. Such inhibition of neuraminidase by Tamiflu and other neuraminidase inhibitors prevents the release of new virus from the infected host cells.

It is observed based on current conditions that the primary challenge in oseltamivir production is the availability of a viable source of shikimic acid. As shikimic acid cannot be synthesized economically, the notion in shortage of shikimic acid has been surfaced due to increasing demand and consequently researchers began bioprospecting in many areas, in their endeavors to find alternative sources apart from star anise seed as briefly mentioned above. Accordingly, shikimic acid content has been discovered in a number of plants, particularly in the seeds of the sweetgum fruit, the Indian plant *Calophylium apetalum* and *Araucaria excelsea*. Nevertheless, it has been observed that these plants produce toxic compounds that necessitate prohibitively expensive refinement methods to ensure and thus obtain purified shikimic acid.

It is being reported that at least 50 million people have been treated with oseltamivir and this amount is expected to increase within the upcoming years. It is further estimated that the market size for Tamiflu will be at 400 million doses per year, at which 130 mg of shikimic acid is required to synthesize one dose of Tamiflu. From here, it can be expected that at least 52 metric tons of shikimic acid is required to meet the upcoming demands. Although production can be increased by way of replacing isolation from plant sources with recombinant microbial catalysts following the need but shortage of shikimic acid will intermittently be a challenging factor especially in the occurrence of a pandemic worldwide.

Following this there is a great need to provide a renewable and inexpensive source or viable alternative sources of shikimic acid.

The commercial value of oil palm (*Elates guineensis*) is in the oil, which offers various health advantages and benefits, owing to its high content of phytonutrients demonstrate antioxidant properties. Nevertheless, at present, the oil palm-based extracts, in particular its vegetation liquour and palm oil mill effluent (POME), has been discovered by way of various studies to have beneficial implications on skin ageing, cancer and heart diseases.

Malaysia is currently one of the world's largest producers of palm oil. Being the major foreign exchange earner industry and to fulfill the rapid progression of the world's demand for palm oil based on the world population growth, Malaysia has at least 265 palm oil mills all over the country.

Typically, the extraction of palm oil which is the primary product of palm fruit, involves a combination of various processes, wherein the main steps include the reception of fresh fruit bunches from plantations, sterilizing and threshing of the bunches, mashing the fruit and pressing the crude palm oil prior to storage and exportation. However, the extraction of palm oil leads to the production of oil palm vegetation liquor which is discarded in the waste stream as Palm Oil Mill Effluent (POME). In addition, Empty Fruit Bunches (EFB) and other waste materials are discarded in the milling process.

Palm oil mill effluent (POME) for instance, if untreated, is a pollutant due to the high chemical oxygen demand (COD) and biological oxygen demand (BOD). The major components of POME include oil and grease and solids, while elements found in POME include phosphorus, potassium, boron, iron, manganese, copper, magnesium and zinc. So far POME has been used in the preparation of fertilizers or as a substrate for bacterial production of biodegradable plastics.

It is being reported that more than 500 kg (around 0.5 m$^3$) of liquid wastes, primarily in the form of palm oil mill effluent (POME), are discharged during the processing of 1.0 metric tons of fresh fruit bunches (Ma et al. 1996) in a typical oil palm mill. Accordingly, it is expected that more than 50 m$^3$ of POME from a mill after processing 100 metric tons of fresh fruit bunches.

Proceeding from the above and based on recent studies on phytochemicals extracted from oil palm, the palm oil industry creates an abundance of prospect in beneficial phytochemicals and other compounds recovery due to the amount of oil palm-based materials including waste materials generated from the industry, if treated effectively.

It is a primary object of the present invention to provide a method for production of shikimic acid based on oil palm extracts.

It is yet another object of the present invention to provide a method for production of shikimic acid based on oil palm by-products.

It is another object of the present invention to provide a composition and a method for producing a composition comprising shikimic acid obtained from oil palm vegetation liquor.

It is yet another object of the present invention to provide a composition and a method for producing shikimic acid obtained from palm oil mill effluent (POME).

It is yet another object of the present invention to provide a composition comprising shikimic acid obtained from extracts from oil palm-based materials and method for producing said shikimic acid based on oil palm-based materials.

It is yet another object of the present invention to provide a composition comprising oil palm phenolics (OPP) with shikimic acid content and method for producing said shikimic acid based on oil palm-based materials.

It is yet a further object of the present invention to provide a composition and method for producing shikimic acid obtained from oil palm liquid waste-based materials.

Further objects and advantages of the present invention may become apparent upon referring to the preferred embodiments of the present invention as shown in the accompanying drawings and as described in the following description.

SUMMARY OF INVENTION

There is disclosed a method for production of shikimic acid comprising the step of obtaining extracts from oil palm-based materials.

It is disclosed that the extracts comprise oil palm phenolics (OPP) obtained from oil palm-based materials.

It is further disclosed that the shikimic acid are purified from the OPP extracts.

It is further disclosed that the OPP extracts are obtained from palm oil vegetation liquor.

It is further disclosed that the OPP extracts are obtained from palm oil mill effluent (POME).

In another aspect of the present invention there is disclosed a composition containing shikimic acid, wherein said shikimic acid is obtained from extracts of oil palm.

BRIEF DESCRIPTION OF THE DRAWING

FIG. 1 shows the HPLC profile (top) and Voyager™ (bottom) for shikimic acid of a sample Oil Palm Phenolics (OPP) extract obtained based on an embodiment of the present invention.

DETAILED DESCRIPTION OF THE INVENTION

In line with the above summary, the disclosed description and examples relates to a composition comprising shikimic acid and method of producing the said shikimic acid based on oil palm-based materials. It shall be apparent however to one skilled in the art that the exemplifications are provided to better elucidate the embodiments of the present invention and therefore should not be construed as limiting the scope of protection.

As briefly described earlier, during oil palm fruit processing, the extraction of palm oil generates a waste stream of vegetation liquor, which is thereby considered as an aqueous phase of the milling process prior to being discarded as palm oil mill effluent (POME) and solid wastes.

In one embodiment of the present invention, a method for producing shikimic acid comprises the steps of obtaining extracts from oil palm-based materials is disclosed. Suitably, it should be noted that oil palm based materials including vegetation liquors, any oil palm by products, palm oil milling wastes materials, oil palm based waste materials (liquid and solid), materials from oil palm based industries, any ancillary oil palm vegetative matters, any part of the oil palm tree for instance but not limiting to the stem, pulp, seed, trunk, fruitlet, fruitbunch, frond, any part of the oil palm fruit and other oil palm based materials and sources not name explicitly herein.

The method further includes the step of obtaining extracts from oil palm-based materials preferably without using solvents.

In one embodiment of the present invention, the method may include the step of obtaining water soluble, and enriched with phenolic compounds, extracts from oil palm-based materials.

In accordance with the present invention, the step of obtaining extracts from oil palm-based materials may be performed based on conventional separation principles. It should be noted that however the method involved for extraction is solvent-free.

According to the present invention, the method may further includes the step of obtaining water soluble, antioxidant rich extracts known as oil palm phenolics (OPP) from oil palm based materials including vegetation liquors, any oil palm by products, palm oil milling wastes materials, materials from oil palm based industries, any ancillary oil palm vegetative matters, any part of the oil palm tree for instance but not limiting to the stem, pulp, seed, trunk, fruitlet, fruitbunch, frond, any part of the oil palm fruit and other oil palm based materials and sources not name explicitly herein.

Based on another embodiment of the present invention, the extracts may be obtained from materials used or generated from oil palm-based industries.

In another embodiment of the present invention, the extraction of the oil palm phenolics (OPP) as briefly described above in accordance with a preferred embodiment of the present invention may involve the steps of providing three-phase decanter system, and preferably a plurality of separation stages using different types of membranes suitably adapted to separate residual oil, ionic contaminants and components of high molecular weight, thereby obtaining oil palm phenolics (OPP).

As an example, oil palm phenolics (OPP) in accordance with an embodiment of the present invention can be obtained from palm oil mill effluent (POME). Generally, palm oil mill effluent (POME) is a thick brownish liquid that contains approximately 4% solids by dry weight. POME can be a source of nutrient content (Zakaria et. al) upon treated to reduce the organic load (Ma et al.). Conventionally, the treated POME may be recycled to the field. In one embodiment of the present invention, shikimic acid is purified from said oil palm phenolics (OPP).

According to the present invention, the method further includes the step of extraction or purifying shikimic acid from the oil palm-based materials extracts.

In accordance with a preferred embodiment of the present invention, preparation of the extracts, oil palm or parts of oil palm may be treated with glyphosate, a compound typically used in eliminating unwanted plants especially weeds, so as to increase levels or obtain high yield of shikimic acid. It is observed that glyphosate inhibits the enzyme EPSP synthase, thus condenses shikimate-3-phosphate and phosphore-enol-pyruvate to form 5-enolpyruvylshikimate-3-phosphate, a precursor of chorismate. It is understood that the dose of glyphosate is suitably controlled to as to allow maximum yield of shikimic acid.

It is understood that the extracts from oil palm-based materials or OPP extracts can be scaled up to accommodate larger or more substantial extraction batch sizes desired.

In order to determine the radical scavenging activity of the OPP prepared for the purpose of the present invention, standard procedures may be carried out. Such may include, but not limiting to, conducting Flash Chromatography or High Performance Liquid Chromatography (HPLC) on the OPP extracts. Results showing the compounds are obtained and presented in chromatograms. A free radical scavenging activity based on the plotted graph of obtained fractions and absorbance may be provided.

As an example, HPLC was carried out on a sample of OPP extracts. Results obtained to show the presence and HPLC profile of shikimic acid are as shown in FIG. 1.

In accordance with a preferred embodiment of the present invention, the determination of elements within the extracts can be carried out using various standard procedures, for instance, but not limiting to, mass spectroscopy.

A Nuclear magnetic resonance (NMR) analysis may further be carried out to confirm such purification.

In an embodiment of the present invention, extraction and purification of shikimic acid from OPP may be conducted based on standard purification methods. Suitably, it is understood that the extract and purification can be scaled up to accommodate larger or more substantial extraction batch sizes desired.

According to the present invention, the yield of shikimic acid obtained from OPP is approximately 1% of the dry weight. It is expected that the amount may increase if plant is treated with glyphosate prior to extracting the OPP.

An example of estimates of the amount of palm oil mill effluent (POME) may be required for production of shikimic acid at different extraction efficiencies are as depicted in TABLE 1 below:

Apart from being the primary building block in the production of Tamiflu, shikimic acid has been reported based on various recent studies, to provide other various health related benefits.

Shikimic acid obtained based on the present invention may be used as an immunomodulatory agent. As an example, in an in-vitro model, incubation of peripheral blood mononuclear cells with shikimic acid in combination with the polyphenol quercetin led to an increase in the release of chemokines IL-8 and IL-6, whereby these chemokines play a major role in recruiting and activating lymphocytes for the innate immunity system. Such discovery therefore demonstrates that shikimic acid and quercetin from dietary may enhance the innate immunity system, which would be beneficial for combating viral infections (Bertelli et al.).

In accordance with the present invention, the shikimic acid obtained may be used in the treatment for hair loss. As an example, an experiment was conducted and water-soluble extracts containing shikimic acid obtained from *Illicium anisatum* (aniseed) has been reported to be able to aid in increasing subcutaneous blood flow and in mice and thus stimulate the elongation of mouse follicles in culture (Sakaguchi et al.).

Further in accordance with the present invention, the OPP extracts containing shikimic acid obtained from oil palm-based materials may be used to make, or are contained in but not limiting to, drinks, edible products, health supplements, antioxidant additives, cosmeceutical products or medicinal products.

From the foregoing it is disclosed that oil palm-based materials can be considered as the most abundant and inexpensive source for shikimic acid. It is estimated that 46 million tons of palm oil mill effluent (POME) can be produced yearly.

It is understood by a person skilled in the art that the methods for experiments and studies are described as exemplifications herein and thus the results are not intended, however, to limit or restrict the scope of the invention in any way and should not be construed as providing conditions, parameters, agents or starting materials which must be utilized exclusively in order to practice the present invention. It is therefore understood that the invention may be practiced, within the scope of the appended claims, with equivalent methods for the experiments than as specifically described and stated in claims.

We claim:

1. A composition containing shikimic acid, wherein said shikimic acid is obtained from extracts of oil palm or oil palm-based materials.

|  | 1 kg | 10% market demand = 5,200 Kg | 50% market demand = 26,000 Kg | 100% market demand = 52,000 Kg |
|---|---|---|---|---|
| 0.1% Shikimic acid yield form dry mass | 25 tons | 132,000 tons | 660,270 tons | 1,320,000 tons |
| 0.5% Shikimic acid yield from dry mass | 5 tons | 26,4000 tons | 132,000 tons | 264,000 tons |
| 1% Shikimic acid yield from dry mass | 2.5 tons | 13,200 tons | 66,000 tons | 132,000 tons |

2. A composition as claimed in claim 1, wherein the extracts comprise of oil palm phenolics (OPP).

3. A composition as claimed in claim 1, wherein said shikimic acid is obtained from palm oil mill effluent (POME).

4. A composition as claimed in claim 1, wherein the shikimic acid is obtained from palm oil vegetation liquor.

* * * * *